(12) United States Patent
Neidrauer et al.

(10) Patent No.: US 10,031,137 B2
(45) Date of Patent: Jul. 24, 2018

(54) DEVICES, METHODS, AND KITS FOR DETECTING AN ANALYTE IN A SAMPLE

(71) Applicants: Michael Neidrauer, Ardmore, PA (US); Michael Kochersperger, Princeton, NJ (US); Nikolay Voznyak, Yardley, PA (US)

(72) Inventors: Michael Neidrauer, Ardmore, PA (US); Michael Kochersperger, Princeton, NJ (US); Nikolay Voznyak, Yardley, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/851,883

(22) Filed: Sep. 11, 2015

(65) Prior Publication Data
US 2015/0377878 A1 Dec. 31, 2015

Related U.S. Application Data

(63) Continuation of application No. PCT/US2014/028226, filed on Mar. 14, 2014.
(Continued)

(51) Int. Cl.
| | |
|---|---|
| *G01N 33/543* | (2006.01) |
| *G01N 33/58* | (2006.01) |
| *B82Y 15/00* | (2011.01) |
| *B01L 3/00* | (2006.01) |
| *G01N 21/64* | (2006.01) |

(52) U.S. Cl.
CPC .. *G01N 33/54386* (2013.01); *B01L 3/502753* (2013.01); *B82Y 15/00* (2013.01); *G01N 33/54313* (2013.01); *G01N 33/588* (2013.01); *B01L 2200/10* (2013.01); *B01L 2300/069* (2013.01); *B01L 2300/0681* (2013.01); *B01L 2300/0816* (2013.01); *B01L 2300/0825* (2013.01); *B01L 2300/0867* (2013.01); *B01L 2400/0406* (2013.01); *G01N 21/645* (2013.01);
(Continued)

(58) Field of Classification Search
None
See application file for complete search history.

(56) References Cited

U.S. PATENT DOCUMENTS

| 5,198,368 A | 3/1993 | Khalil et al. |
| 5,441,894 A | 8/1995 | Coleman et al. |

(Continued)

FOREIGN PATENT DOCUMENTS

WO  WO2012068709 A1  5/2012

OTHER PUBLICATIONS

International Search Report and Written Opinion, PCT/US2014/028226, Jul. 28, 2014.
(Continued)

*Primary Examiner* — Rebecca L Martinez
(74) *Attorney, Agent, or Firm* — Saul Ewing Arnstein & Lehr LLP; Kathryn Doyle; Brian R. Landry

(57) ABSTRACT

One aspect of the invention provides a device for detecting an analyte in a sample. The device includes: a sample loading region, an imaging window, a well, and an absorbent pad. The sample loading region is in fluid communication with the well. The well is in fluid communication with the absorbent pad, such that when a fluid sample comprising solid support structures and a liquid carrier are applied to the sample loading region, the fluid sample travels to the well and at least part of the liquid carrier is absorbed into the absorbent pad.

13 Claims, 9 Drawing Sheets

Related U.S. Application Data

(60) Provisional application No. 61/794,288, filed on Mar. 15, 2013.

(52) U.S. Cl.
CPC . *G01N 21/6489* (2013.01); *G01N 2021/6441* (2013.01); *G01N 2021/6482* (2013.01); *G01N 2333/4712* (2013.01)

(56) References Cited

U.S. PATENT DOCUMENTS

| | | |
|---|---|---|
| 2010/0267055 A1 | 10/2010 | Konrath |
| 2010/0267167 A1 | 10/2010 | Day et al. |
| 2011/0256638 A1 | 10/2011 | Chan et al. |
| 2012/0010094 A1 | 1/2012 | Spinale et al. |

OTHER PUBLICATIONS

Agarawal, A., et al., 2007, "Single-Bead Immunoassays Using Magnetic Microparticles and Spectral-Shifting Quantum Dots", J. Agric. Food Chem. 55, 3778-3782.

Bangs Laboratories, Inc., 2012, "Microsphere Selection—How to choose which bead to use!", http://www.bangslabs.com/learning/microsphere_selection, 1-2.

Gao. R., et al., 2008, "Single-Bead-Based Immunofluorescence Assay for Snake Venom Detection", Biotechnol. Prog., 24, 245-249.

Zhang, B., et al., 2009, "Quantum dots/particle-based immunofluorescence assay: Synthesis, characterization and application", Journal of Photochemistry and Photobiology B: Biology, 94, 45-50.

DEVICES, METHODS, AND KITS FOR DETECTING AN ANALYTE IN A SAMPLE

CROSS-REFERENCE TO RELATED APPLICATIONS

This application is a continuation of International Application No. PCT/US2014/028226, filed Mar. 14, 2014, which claims priority to U.S. patent application Ser. No. 61/794,288, filed Mar. 15, 2013. The entire content of these applications is hereby incorporated by reference herein.

BACKGROUND OF THE INVENTION

The chemiluminescence based enzyme linked immunosorbent assay (ELISA) has become a standard immunoassay technique in the laboratory. However, ELISA requires a relatively large volume of sample (~50 µL) in order to detect an analyte at picomolar concentrations. Furthermore, ELISA, along with other immunoassay techniques, requires the use of non-specific binding methods and agents, such as horseradish peroxidase, in order to detect the analyte of interest.

Quantum dot-linked immunosorbent assay (QLISA) is an alternative technique where antibodies are conjugated to fluorescent nanoparticles (quantum dots) for detection and quantitation of the desired analyte. QLISA provides detection of an analyte at picomolar concentrations at sample volumes within the range of about 1 µL to about 5 µL, which is about a ten-fold decrease in sample volume as compared to ELISA. Moreover, in QLISA, the antibody for capturing an analyte of interest is covalently bound to the substrate, as opposed to non-specific binding methods used in traditional ELISA or other immunoassay techniques.

Techniques have been developed to perform the QLISA assay using analytes conjugated to solid supports suspended in a fluid medium, such as a liquid sample. However, prior to detection of the analyte from a liquid sample, the solid supports must be separated from the liquid in order to reduce the volume of the sample. A reduced sample volume ensures that all of the quantum dots can be excited using a focused beam of light and detected, thus ensuring the most accurate quantification method possible. Generally, the solid supports are filtered and then transferred into a holder for imaging and detection. Unfortunately, this transfer step may result in the loss of some of the spheres, thereby diminishing the accuracy of the results.

SUMMARY OF THE INVENTION

One aspect of the invention provides a device for detecting an analyte in a sample. The device includes: a sample loading region, an imaging window, a well, and an absorbent pad. The sample loading region is in fluid communication with the well. The well is in fluid communication with the absorbent pad, such that when a fluid sample comprising solid support structures and a liquid carrier are applied to the sample loading region, the fluid sample travels to the well and at least part of the liquid carrier is absorbed into the absorbent pad.

This aspect of the invention can have a variety of embodiments. The amount of analyte in the sample can be quantified. The device can include a plurality of sample loading regions. The plurality of sample loading regions can be in fluid communication with the well.

Another aspect of the invention provides a method for detecting at least one analyte in a fluid sample. The method includes: adding a labeled moiety to a fluid sample; suspending solid support substrates conjugated to an unlabeled moiety in the fluid sample; capturing the solid support substrates in a reduced sample volume; and detecting the labeled moiety in the region of the captured solid support substrates when an analyte is present in the sample. The presence of the labeled moiety in the region of the captured solid support substrates is indicative of both the labeled and unlabeled moieties binding to the analyte.

This aspect of the invention can have a variety of embodiments. The sample volume can be reduced by an absorbent pad removing at least a portion of a carrier liquid from the sample. The label can be a quantum dot. The amount of analyte can be quantified.

The method can further include detecting the presence of a plurality of analytes in the sample via a plurality of uniquely labeled moieties and a plurality of unlabeled moieties conjugated to the support substrates. The unique labels can be different sized quantum dots.

The solid support substrates can be microspheres. The microspheres can be selected from the group consisting of polystyrene (PS) microspheres, poly(methyl methacrylate) (PMMA) microspheres, silica microspheres, glass microspheres, ceramic microspheres, magnetic microspheres, and paramagnetic microspheres.

The solid support substrates can be nanospheres. The nanospheres can be selected from the group consisting of polystyrene (PS) nanospheres, poly(methyl methacrylate) (PMMA) nanospheres, silica nanospheres, glass nanospheres, ceramic nanospheres, magnetic nanospheres, and paramagnetic nanospheres.

Another aspect of the invention provides a kit including the device as described herein and one or more of (a) a moiety conjugated to a label, (b) a solid support substrate conjugated to a label, or (c) a reagent for conjugating a label to a moiety or solid support substrate.

This aspect of the invention can have a variety of embodiments. The reagent can comprise Ethyl-3-(dimethylaminopropyl)carbodiimide(EDAC) or 4-(maleimidomethyl)-1-cyclohexanecarboxylic acid N-hydroxysuccinimide ester (SMCC). The label can be a quantum dot.

The moiety can be one or more of an antibody, peptidomimetic, polypeptide, aptamer, or nucleic acid.

The solid support substrate can be a microsphere or nanosphere. The microsphere can be selected from the group consisting of polystyrene (PS) microspheres, poly(methyl methacrylate) (PMMA) microspheres, silica microspheres, glass microspheres, ceramic microspheres, magnetic microspheres, and paramagnetic microspheres. The nanosphere can be selected from the group consisting of polystyrene(PS) nanospheres, poly(methyl methacrylate)(PMMA) nanospheres, silica nanospheres, glass nanospheres, ceramic nanospheres, magnetic nanospheres, and paramagnetic nanospheres.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A depicts the exterior housing of the apparatus, while FIG. 3B is an exploded view of the basic components of the apparatus.

FIG. 3C provides an exploded view of the basic components of the apparatus, while FIG. 3D depicts the exterior housing of the apparatus.

FIG. 4A depicts the exterior housing of the apparatus, while FIG. 4B depicts the internal components of the apparatus.

DETAILED DESCRIPTION

Figure 1:
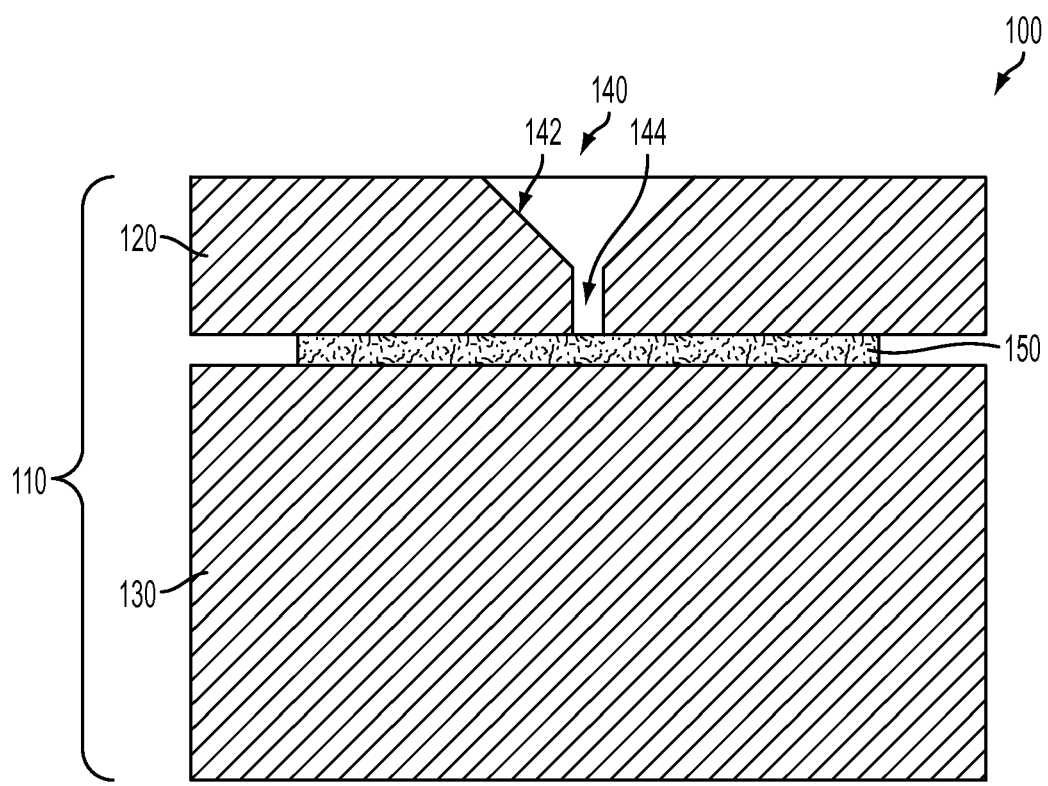
FIG. 1 is a crossection of an exemplary imaging apparatus, in accordance with the present invention.

There is a need for an apparatus for the quantification of microspheres that provides both sample concentration and imaging without the need for an additional transferring step. The present invention satisfies this need.

As contemplated herein, the present invention relates to an apparatus and a method for detecting and quantifying analytes conjugated to a substrate comprising solid support structures suspended in a fluid medium.

For example, an apparatus according to the invention includes a housing that holds a suspension of the solid support structures in a liquid sample in which one or more analytes conjugated to the solid support structures have been further conjugated with quantum dots, and concentrates the solid support structures into a small volume compartment or plug by wicking away or removing the liquid. The concentrated support structures can then be imaged via a light source that energizes the quantum dots and a camera system for detecting and quantifying the concentrated quantum dots. A method of using an apparatus according to the invention can include the steps of collecting a sample, conjugating analytes in the sample to solid support structures suspended in the sample, conjugating quantum dots to the analytes, energizing the quantum dots with a light source, detecting emission from the quantum dots, and determining the concentration of the analyte in the sample based on a correlation between detected emission and analyte concentration. In particular, methods disclosed herein can use monoclonal antibodies conjugated to quantum dots as a means of detecting nano-levels of analytes. As used herein, the methods have collectively been dubbed "Quantum-Linked ImmunoSorbent Assay" (QLISA) as differentiated from the technique known in the art as Enzyme-Linked ImmunoSorbent Assay (ELISA).

It is to be understood that the figures and descriptions of the present invention have been simplified to illustrate elements that are relevant for a clear understanding of the present invention, while eliminating, for the purpose of clarity, many other elements found in typical analyte detection assays. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. It should be appreciated that the disclosure herein is directed to all such variations and modifications to such elements and methods known to those skilled in the art.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "analyte" as used herein is a broad term and is used in its ordinary sense, including, without limitation, to refer to a detectable component of a sample, such as a substance or chemical constituent in a biological liquid (for example, blood, interstitial liquid, cerebral spinal liquid, lymph liquid or urine). Analytes can include naturally occurring substances, artificial substances, metabolites, and/or reaction products.

The term "solid support", "support structure", and "substrate" as used herein are used interchangeably and refer to a material or group of materials having a rigid or semi-rigid surface or surfaces. There is no limitation to the shape or size of the support structures. In many embodiments, the solid support(s) will take the form of beads (e.g., silica beads, magnetic beads, paramagnetic beads, and the like), resins, gels, microspheres, or other geometric configurations.

The term "antibody" refers to an immunoglobulin molecule which is able to specifically bind to a specific epitope on an antigen. Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies. As contemplated herein, an antibody conjugated to a quantum dot and support structure may specifically or non-specifically recognize and/or bind to an analyte, such that the analyte can be analyzed qualitatively and quantitatively.

A "biological sample" refers to any sample comprising a cell, a tissue, or a bodily liquid obtained from an organism in which expression of a biomarker can be detected. An example of such a biological sample includes, but is not limited to blood, lymph, urine, gynecological liquids, biopsies, amniotic liquid, stool samples, fecal samples, and smears. Samples that are liquid in nature are referred to herein as liquid samples or fluid samples.

The term "quantum dot" (QD) refers to a semiconductor nanostructure that confines the motion of conduction band electrons, valence band holes, or excitons (bound pairs of conduction band electrons and valence band holes) in all three spatial directions. The confinement can be due to electrostatic potentials (generated by external electrodes, doping, strain, impurities), the presence of an interface between different semiconductor materials (e.g. in core-shell nanocrystal systems), the presence of the semiconductor surface (e.g. semiconductor nanocrystal), or a combination of these. A quantum dot has a discrete quantized energy spectrum. The corresponding wave functions are spatially localized within the quantum dot, but extend over many periods of the crystal lattice. A quantum dot contains a small finite number (of the order of 1-100) of conduction band electrons, valence band holes, or excitons, i.e., a finite number of elementary electric charges. One of the optical features of small excitonic quantum dots immediately noticeable to the unaided eye is coloration. While the material which makes up a quantum dot defines its intrinsic energy signature, more significant in terms of coloration is the size. The larger the dot, the redder (the more towards the red end of the spectrum) the fluorescence. The smaller the dot, the bluer (the more towards the blue end) it is. The coloration is directly related to the energy levels of the quantum dot. Quantitatively speaking, the bandgap energy that determines the energy (and hence color) of the fluoresced light is inversely proportional to the square of the size of the quantum dot.

The term "conjugate" refers to a physical or chemical attachment of one molecule to a second molecule.

The term "specifically binds" refers to an action of a molecule, such as an antibody, which recognizes and binds to a molecule or feature, but does not substantially recognize or bind other molecules or features in a sample.

The terms "patient," "subject," "individual," and the like are used interchangeably herein, and refer to any animal amenable to the methods described herein. In certain non-limiting embodiments, the patient, subject or individual is a human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Separation Device or Apparatus

Referring now to FIG. 1, the present invention includes an imaging apparatus suitable for the imaging and quantification of an analyte conjugated to a solid support suspended in a fluid medium. As shown in FIG. 1, the present invention includes an apparatus 100 having a two-piece housing 110 comprising a top piece 120 and a bottom piece 130, which come together to form housing 110. Top and bottom pieces 120 and 130 can be detachably assembled to form housing 110, or they can be permanently assembled, such as in a disposable embodiment. Top and bottom pieces 120 and 130 can further form a seal, if desired. Top piece 120 can include a well 140, and an absorbent pad 150 can be positioned between at least a portion of top and bottom pieces 120 and 130, such that at least a portion of absorbent pad 150 is exposed to or in fluid contact with well 140. Well 140 can pass through the top and bottom surface of top piece 120, and further can comprise a funnel 142 and a channel 144.

Housing 110 and well 140 can be any desired size and shape, and accordingly, there is no limitation to the particular size and shape of top and bottom pieces 120 and 130, or to well 140. In other embodiments, housing 110 can be a single piece unit, and other embodiments, it can be comprise three or more component pieces. Housing 110 can further include any additional attachment means, including a clamping mechanism, such as hinging clamps or screws positioned on the sides of top and bottom pieces 120 and 130 for tightening the apparatus and improving the seal. Further, well can may be conical, cylindrical, or any other desired shape. It should be appreciated that the size and shape of apparatus 100 can be any size and shape suitable for liquid from the liquid sample containing the solid support suspension to flow from funnel 142 through channel 144 and be absorbed into absorbent pad 150, such that the solid support structures can be consolidated and/or concentrated at least in channel 144 or otherwise within well 140.

Figure 2:
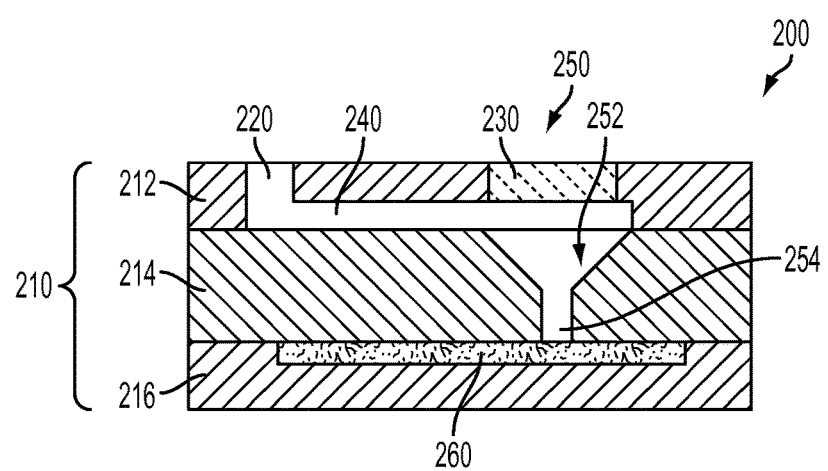
FIG. 2 is a crossection of another exemplary imaging apparatus, in accordance with the present invention.

Referring now to FIGS. 2 and 3, another embodiment of a separation device is illustrated. As shown in FIGS. 2 and 3, a separation device 200 includes a three-piece housing 210 (comprising top piece 212, middle piece 214 and bottom piece 216) with a sample loading region 220 and an imaging window 230. Inside housing 210 is channel 240 fluidly connecting sample loading region 220 to well 250. Window 230 provides an opening through which the plug of the solid support structures collected in well 250 can be viewed for excitation of the quantum dot labels and imaging thereof. In some embodiments, imaging window 230 can further comprise a transparent cover, which can be made of, for example, glass or a polymer material. In other embodiments, imaging window 230 can further comprise a filter useful in imaging, such as a bandpass filter. Well 250 can further comprise a funnel 252 and channel 254 in a similar manner as described in FIG. 1 and can pass through the top and bottom surfaces of middle housing piece 214.

Figure 3A:
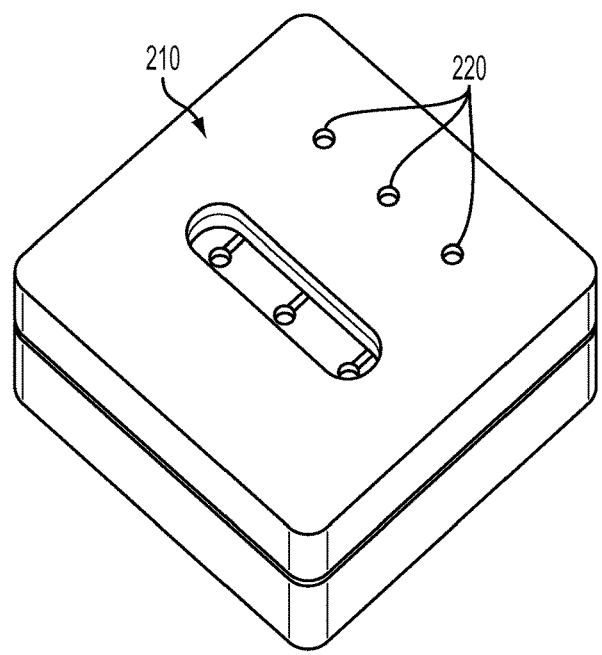
FIGS. 3A and 3B provide perspective views of another exemplary imaging apparatus, in accordance with the present invention.
Figure 3B:
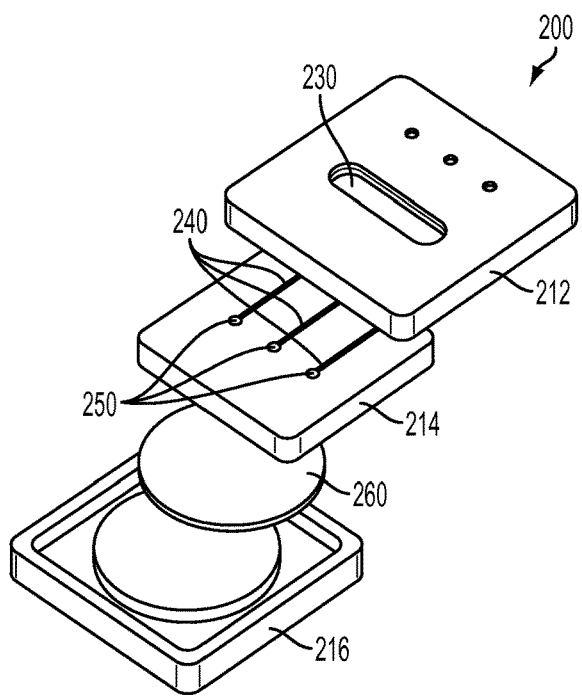
Figure 3C:
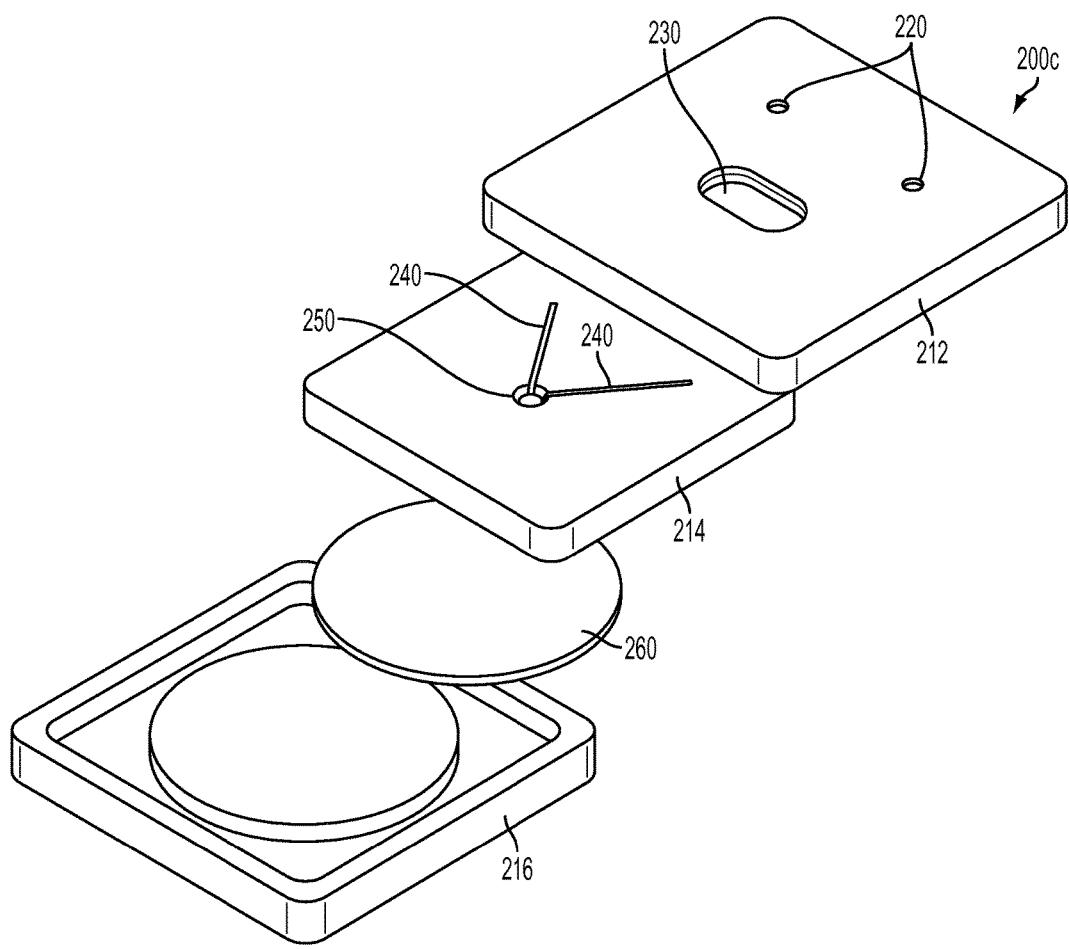
FIGS. 3C and 3D provide perspective views of another exemplary imaging apparatus, in accordance with the present invention.
Figure 3D:
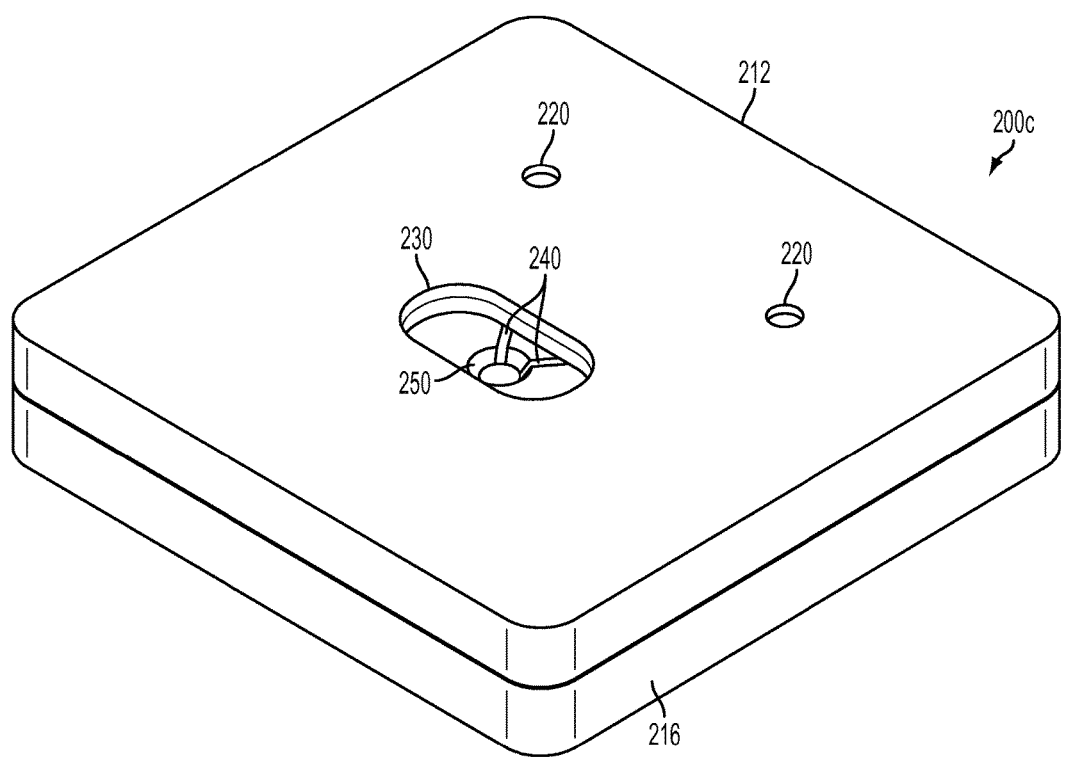

Device 200 can also include an absorbent pad 260. Absorbent pad 260 can be pressed between middle housing pieces 214 and 216, and can rest in a recessed area of housing piece 216 or can sit on a surface above a recessed area as depicted in FIG. 3B. The actual positioning of absorbent pad 260 is not limiting. However, at least a portion of absorbent pad 260 should be in fluid contact with the bottom opening of well 250, such as with the bottom opening of well channel 254.

Similar to the embodiment of FIG. 1, there is no limitation to the size and shape or other dimension of any particular component of device 200, provided that a liquid sample containing the suspended and labeled solid support structures can be applied to device 200 at sample loading region 220 and the sample can flow through channel 240 to well 250, where the liquid carrier of the sample can be absorbed by absorbent pad 260, thereby concentrating the solid support in at least well channel 254 and viewable via imaging window 230.

Figure 4A:
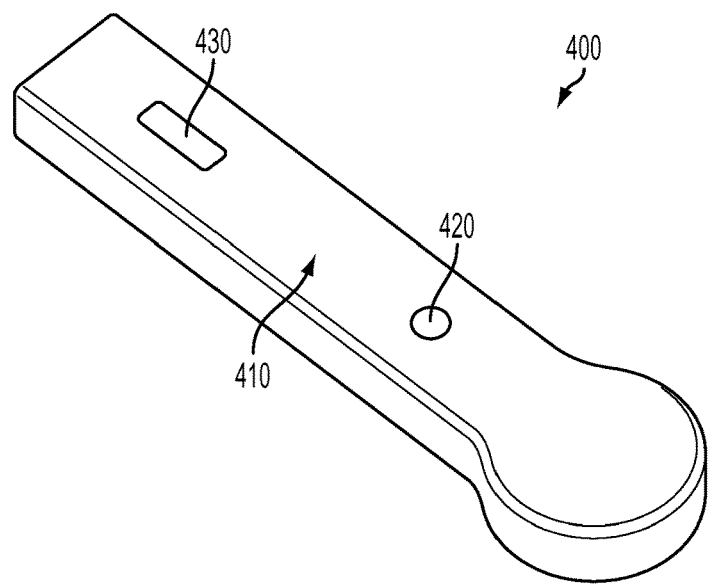
FIGS. 4A and 4B provide perspective views of another exemplary imaging apparatus in accordance with the present invention.
Figure 4B:
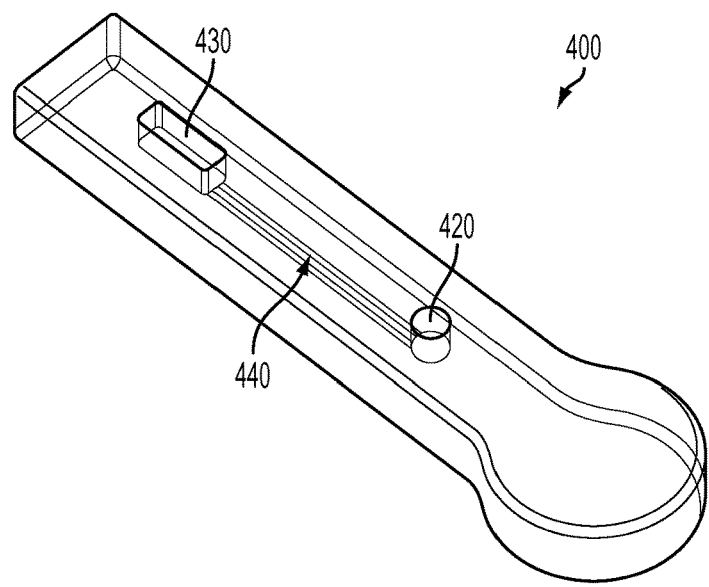

For example, FIG. 4 shows yet another embodiment of a separation and imaging device, according to the present invention. FIG. 4 shows a device 400 comprising a housing 410 with a sample loading region 420 and an imaging window 430. Inside housing 410 is a channel 440 and a well (not shown). Channel 440 fluidly connects sample loading region 420 to the well in a manner similar to that as illustrated in the embodiments of FIGS. 2 and 3.

In some embodiments, sample loading region 420 can be positioned at an end of device 400 in order to permit dipping of the device and sample loading region 420 into a sample.

As depicted in FIG. 3, device 200 may comprise a set of sample loading regions, where each sample loading region includes its own channel leading to its own well. In such embodiments, a single device 200 can be suitable for multiple testing runs, or combinations of assay types, as desired.

Referring now to FIGS. 2C and 2D, a well 250 can optionally be in fluid communication with a plurality of channels 240. Such an arrangement allows for multiple substances (e.g., samples, reagents, solvents, and the like) to be introduced into separate sample loading regions 220 before mixing and imaging in well 250. Such an arrangement advantageously enables on-board chemical and/or biological reactions prior to or during imaging.

The separation device 200c depicted in FIGS. 2C and 2D can be used in a variety of manners. In one embodiment, the user can prime all channels with fluid, then occlude any unused channels (e.g., with a sealant, plug, tape, and the like) to prevent back flow into any non-selected channels. The user could then flow liquid into the selected channel. Further channels can be sequentially loaded in the same manner.

All housing pieces can be formed from any material including, but not limited to, a polymer, a glass, a metal, a ceramic material, or a combination thereof. In one embodiment, one or more of the housing pieces are formed from black DELRIN® acetal resin available from E. I. du Pont de Nemours and Company of Wilmington, Del. In one embodiment, the housing is a single-use, disposable component. In another embodiment, only a portion of the housing is a disposable component. In another embodiment, one or more of the housing pieces may be made of an autoclavable material. Examples of autoclavable materials include, without limitation, glass, polypropylene, polymethylpentene, polycarbonate, acetal products, and polysulfone products.

Liquid Sample and Suspension

As mentioned elsewhere herein, the devices of present invention can be used for any imaging analysis where the collection and concentration of a labeled solid support suspended in a fluid medium is desired. The present invention is uniquely structured for the concentration of the solid support by allowing the solid support to travel to a collection region and subsequently wicking away liquid surrounding the suspension of the solid support.

As contemplated herein, the solid support can be any solid support that is suspendable in a fluid medium, as would be understood by those having ordinary skill in the art. In some embodiments, the solid support is a microsphere or a nanosphere. Microspheres and nanospheres advantageously have a large surface area per unit volume.

Non-limiting examples of microspheres include polystyrene (PS) microspheres, poly(methyl methacrylate) (PMMA) microspheres, silica microspheres, glass microspheres, and ceramic microspheres. In certain embodiments, the microspheres are silica microspheres. The diameter of the microsphere can range from 0.5 µm to 5 µm, but are not limited to such dimensions. In one embodiment, the diameter of the microsphere is 1 µm.

In some embodiments, the diameter of a nanosphere can be less than about 1 µm. In other embodiments, the diameter of a nanosphere can be between about 40 nm and about 950 nm, between about 200 nm and about 950 nm, and the like.

In some embodiments, the microsphere is conjugated to a first antibody that specifically binds to an analyte. In such cases, a second antibody that is conjugated to a quantum dot, where the second antibody also specifically binds to the analyte. Thus, when the support structure-first antibody complex and the second antibody labeled by the quantum dot are added to a sample containing the analyte, both the first and second antibodies bind to the analyte and allow for the collection and concentration of the complex for imaging.

Binding of QD Conjugates to Analytes

One method of measuring the concentration of an analyte in a sample is to conjugate QDs to the analyte and then to detect and quantify the presence of the QDs by fluorescence. The conjugation of QDs to a analyte can be done by conjugating a QD to an intermediary, such as a targeting moiety, which is selected based on its ability to specifically bind to an analyte of interest.

A QD conjugate comprises at least one quantum dot (i.e., a semiconductor nanocrystal) that can be detected by means of its fluorescent properties. Quantum dots are ultra-sensitive non-isotopic reporters of biomolecules in vitro and in vivo. QDs are attractive fluorescent tags for biological molecules due to their large quantum yield and photostability. As such, QDs overcome many of the limitations inherent to the organic dyes used as conventional fluorophores. QDs range from 2 nm to 10 nm in diameter, contain approximately 500-1000 atoms of materials such as cadmium and selenium, and fluoresce with a broad absorption spectrum and a narrow emission spectrum.

A water-soluble luminescent QD, which comprises a core, a cap and a hydrophilic attachment group is well known in the art and commercially available (e.g. Quantum Dot Corp. Hayward, Calif.; Invitrogen, Carlsbad, Calif.; U.S. Pat. Nos. 7,192,785; 6,815,064). The core comprises a nanoparticle-sized semiconductor. While any core of the IIB VIB, IIIB VB or IVB-IVB semiconductors can be used, the core must be such that, upon combination with a cap, a luminescence results.

The cap or shell is a semiconductor that differs from the semiconductor of the core and binds to the core, thereby forming a surface layer on the core. The cap must be such that, upon combination with a given semiconductor core, a luminescence results. Two of the most widely used commercial QDs come with a core of CdSe or CdTe with a shell of ZnS and emissions ranging from 405 nm to 805 nm.

The attachment group refers to any organic group that can be attached, such as by any stable physical or chemical association, to the surface of the cap of the QD. In one embodiment, the attachment group can render the QD water-soluble without rendering the QD no longer luminescent. Accordingly, the attachment group comprises a hydrophilic moiety. In one aspect, the attachment group may be attached to the cap by covalent bonding and is attached to the cap in such a manner that the hydrophilic moiety is exposed. Suitable hydrophilic attachment groups include, for example, a carboxylic acid or salt thereof, a sulfonic acid or salt thereof, a sulfamic acid or salt thereof, an amino substituent, a quaternary ammonium salt, and a hydroxy. In another aspect, QD may be rendered water soluble by capping the shell with a polymer layer that contains a hydrophobic segment facing inside towards the shell and a hydrophilic segment facing outside. The hydrophilic layer can be modified to include functional groups such as —COOH and —$NH_2$ groups for further conjugation to proteins and antibodies or oligonucleotides as described in Chan and Nie, 1998, (Science 281:2016-8), Igor et al., 2005, (Nature Materials 4:435-46), Alivisatos et al., 2005, (Annu. Rev. Biomed. Eng. 7:55-76) and Jaiswal et al., 2003, (Nature Biotech. 21:47-51) and incorporated herein in their entirety by reference.

A QD can be conjugated to a targeting moiety. The targeting moiety specifically binds to the analyte of interest and may comprise an antibody, a peptidomimetic, a polypeptide or aptamer, a nucleic acid or any other molecule provided it binds specifically to a biomarker of interest. When the targeting moiety comprises an antibody, the antibody preferably specifically binds to the analyte of interest.

In another embodiment, the QD may be conjugated to a targeting moiety comprising a nucleic acid binding moiety. The nucleic acid binding moiety may comprise any nucleic acid, protein, or peptide that binds to nucleic acids, such as a DNA binding protein. A preferred nucleic acid is a single-stranded oligonucleotide comprising a stem and loop structure and the hydrophilic attachment group is attached to one end of the single-stranded oligonucleotide.

The antibody or nucleic acid can be attached to the QD, such as by any stable physical or chemical association, directly or indirectly by any suitable means. Quantum dot conjugation may be achieved by a variety of strategies that include but are not limited to passive adsorption, multivalent chelates or classic covalent bond formation described in Jaiswal et al., 2003 (Nature Biotechnol. 21:47-51) and incorporated by reference herein.

In another embodiment, the QD may be conjugated to the solid support, and the solid support may be conjugated to a targeting moiety, such as an antibody, a peptidomimetic, a polypeptide or aptamer, a nucleic acid or any other molecule provided it binds specifically to an analyte of interest. In such embodiments, the separation and imaging device, as described elsewhere herein, may include a second targeting moiety that specifically binds to the analyte of interest, and is further immobilized on a surface in the device well such that when the immobilized moiety binds the analyte-antibody-solid support-QD complex, the QD can be visualized by the detection system through the imaging window of the device.

The covalent bond formation is the simplest in execution and hence widely used for conjugation. The antibody or nucleic acid is attached to the attachment group directly or indirectly through one or more covalent bonds. If the antibody is attached indirectly, the attachment preferably is by means of a "linker," i.e., any suitable means that can be used to link the antibody or nucleic acid to the attachment group of the water-soluble QD. The linker should not render the water-soluble QD water-insoluble and should not adversely affect the luminescence of the QD. Also, the linker should not adversely affect the function of the attached antibody or nucleic acid. If the conjugate is to be used in vivo, desirably the linker is biologically compatible. Crosslinkers, e.g. intermediate crosslinkers, can be used to attach an antibody to the attachment group of the QD. Ethyl-3-(dimethylaminopropyl) carbodiimide (EDAC) is an example of an intermediate crosslinker. Other examples of intermediate crosslinkers for use in the present invention are known in the art. See, e.g., Bioconjugate Techniques (Academic Press, New York, (1996)).

In one embodiment, amine groups on QDs are treated with a malemide group containing a crosslinker molecule. These "activated" QDs can be then be directly conjugated to a whole antibody molecule. However the direct conjugation may result in steric hindrance restricting access of the antibody to the analyte of interest. In those instances where a short linker could cause steric hindrance problems or otherwise affect the functioning of the targeting moiety, the length of the linker can be increased, e.g., by the addition of from about a 10 to about a 20 atom spacer, using procedures well-known in the art. One possible linker is activated polyethylene glycol, which is hydrophilic and is widely used in preparing labeled oligonucleotides.

The Stretptavidin Biotin reaction provides another conjugation method where the biotinylated protein/biomolecule is attached to a streptavidin coated QD.

One of skill in the art will appreciate that it may be desirable to detect more than one analyte in a biological sample. Therefore, in particular embodiments, at least two antibodies directed to two distinct analytes are used. Where more than one antibody is used, these antibodies may be added to a single sample sequentially as individual antibody reagents or simultaneously as an antibody cocktail. Alternatively, each individual antibody may be added to a separate sample from the same source, and the resulting data pooled.

Quantum dots are conjugated to antibody fragments using a heterobiofunctional crosslinker 4-(maleimidomethyl)-1-cyclohexanecarboxylic acid N-hydroxysuccinimide ester (SMCC). The commercial Quantum dots (Invitrogen Corporation, Carlsbad, Calif.) come with —NH2 groups on their surface. These amino groups are reacted with the crosslinker SMCC to create malemide groups on the QDs surface. Antibodies of interest are reduced by DTT (Dithiothreitol) and disulfide bonds are broken to create thiol(—SH) groups. The final conjugation relied on the covalent bond formed between the malemide group on activated QDs and the thiol group on the antibodies. The ratio of antibody conjugated to QDs is 1:4 and the typical yield of the reaction at the end of conjugation procedure is anywhere between 500 µl to 800 µl.

Table I presents a list of QDs conjugated to antibodies using the procedure outlined above:

TABLE 1

Different color QDs conjugated to various antibodies.

| Quantum Dots | Antibodies | Stock Concentration |
| --- | --- | --- |
| QD565 | MPO (Santa Cruz BT) | 1.2 µM |
| QD655 | MPO (Santa Cruz BT) | 500 nM |
| QD655 | Anti-Testosterone | 1.5 µM |
| QD605 | Anti-TNFα | 1 µM |
| QD705 | Anti-TNFα | 1.2 µM |
| QD605 | Anti-IL-1α | 1.5 µM |
| QD705 | Anti-IL-1α | 1.5 µM |

Detection Using QD as Fluorophores

Given the disclosure set forth herein, the skilled artisan will understand how to use any methods available in the art for identification or detection of an analyte, such as a protein, nucleic acid, or a biomolecule of interest. Methods for detecting an analyte comprise any method that determines the quantity or the presence of the analyte.

In one embodiment, the method comprises contacting the sample with a QD-first antibody conjugate, wherein the antibody of the conjugate specifically binds to the analyte, contacting the analyte with a solid support-second antibody conjugate, wherein the antibody of the conjugate specifically binds to the analyte, concentrating the QD-first antibody-analyte-second antibody-solid support complex, and detecting fluorescence, wherein the detection of fluorescence indicates that the analyte is present in the sample.

In another embodiment, the method comprises contacting the sample with a QD-solid support-first antibody conjugate, wherein the antibody of the conjugate specifically binds to the analyte, immobilizing a second antibody to a surface of the device in a location visible in the imaging window, wherein the second antibody specifically binds to the analyte, thereby capturing the QD-solid support-first antibody-analyte-complex and detecting fluorescence, wherein the detection of fluorescence indicates that the analyte is present in the sample.

The present invention also provides a method whereby two or more different target analytes can be simultaneously detected in a sample. The method involves using a set of QD conjugates, wherein each of the conjugates in the set has a differently sized QD or a QD of different composition attached to an antibody that specifically binds to a different analyte in the sample. In an embodiment, the QD of the conjugates range in size from 2 nm to 6.5 nm, which sizes allow the emission of luminescence in the range of blue to red. The QD size that corresponds to a particular color emission is well-known in the art. Within this size range, any size variation of QD can be used as long as the differently sized QD can be excited at a single wavelength and differences in the luminescence between the differently sized QD can be detected. In another embodiment, the differently sized QD have a capping layer that has a narrow and symmetric emission peak. Similarly, QD of different composition or configuration will vary with respect to particular color emission. Any variation of composition between QD can be used as long as the QD differing in composition can be excited at a single wavelength and differences in the luminescence between the QD of different composition can be detected. Detection of the different analytes in the sample arises from the emission of multicolored luminescence generated by the QD differing in composition or the differently sized QD of which the set of conjugates is comprised. This method also enables different functional domains of one or more single proteins, for example, to be distinguished.

QLISA Methods

The separation and imaging devices as described herein may be useful for imaging and quantifying an analyte through the use of QLISA technology. One of skill in the art will further appreciate that any or all steps in the methods of the invention could be implemented by personnel or, alternatively, performed in an automated fashion. Thus, the steps of sample preparation, labeled complex concentration, and detection of one or more analytes may be automated.

Figure 5:
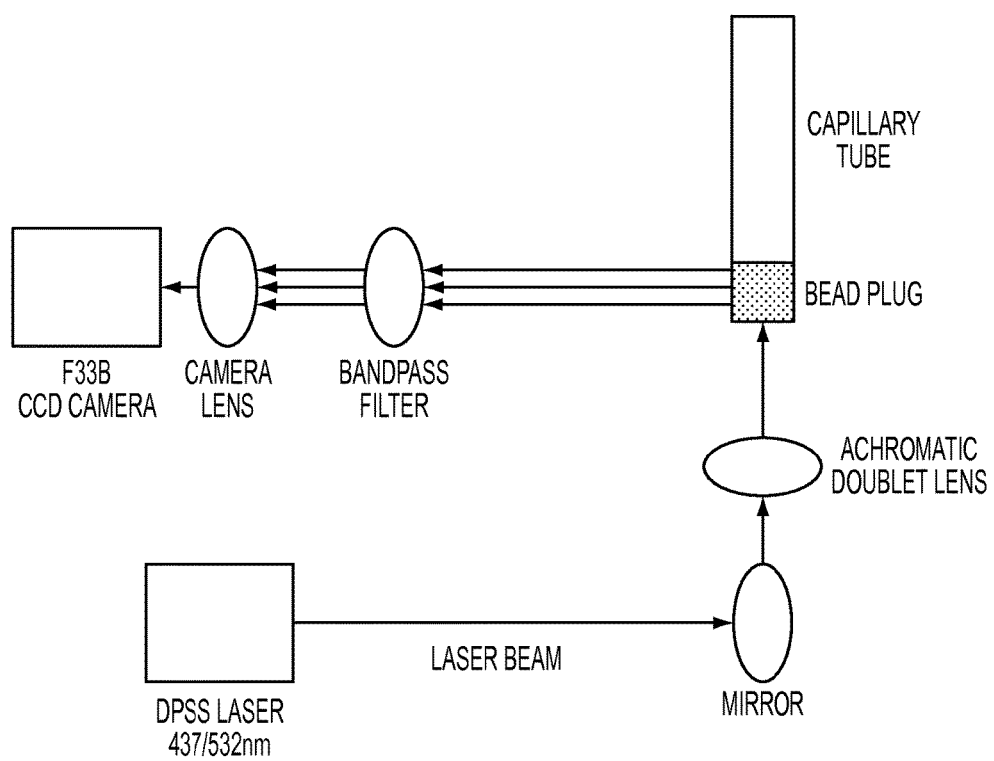
FIG. 5 is a schematic of an imaging assembly, in accordance with the present invention.

According in one embodiment depicted schematically in FIG. 5, the apparatus comprises an imaging apparatus of the present invention for holding a sample to be analyzed, a detection system comprising a laser diode or equivalent light source, with or without a mirror and with or without or without an achromatic doublet lens, to provide an excitation energy to QD conjugates bound to antigens in the sample; and a detection system including an photodetector, a camera lens, and a bandpass filter to improve signal-to-noise ratio. The mirror disposed around at least a portion of an imaging apparatus of the present invention increases the amount of the fluorescent energy emitted by the quantum dots that can be detected by the photodetector. In one embodiment, the light source is a green laser. In another embodiment, the light source is a blue laser. In yet another embodiment, a plurality of laser diodes is used. In an alternative embodiment, the light source is an ultraviolet LED. Non-limiting examples of a photodetector include a charge-coupled device (CCD) camera, a time delay integration (TDI) camera, a spectrometer coupled to at least one photomultiplier tube, and an avalanche photodiode detector. In one embodiment, the photodetector is a CCD camera.

A person of skill in the art of ELISA measurements and other similar diagnostic techniques will be familiar with sandwich and competitive assay techniques, so further detailed explanation is not deemed necessary. Using a QLISA apparatus as provided herein, QD conjugates can reliably detect and measure analytes of interest, which can readily be correlated with disease activity indices. These assays are of value and use to a variety of conditions requiring quantification of any analyte of interest.

In one method using an apparatus as disclosed herein, the QLISA method is performed prior to the addition of the sample to the separation and imaging device. The sample is added to the device through the sample loading region as a suspension of solid support structures in a liquid carrier medium, whereupon the solid support suspension flows through the channel and into the well. The solid support structures are collected within the well and the liquid flows through well via a wicking mechanism into the adsorbent pad. The now concentrated solid support structures are imaged and the presence and/or amount of analyte is determined. In another embodiment of the method, one or more analytes and/or other reagents are conjugated to an immobilized surface of the device, as would be understood by those skilled in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Quantification of Troponin I in a Sample

Figure 6:
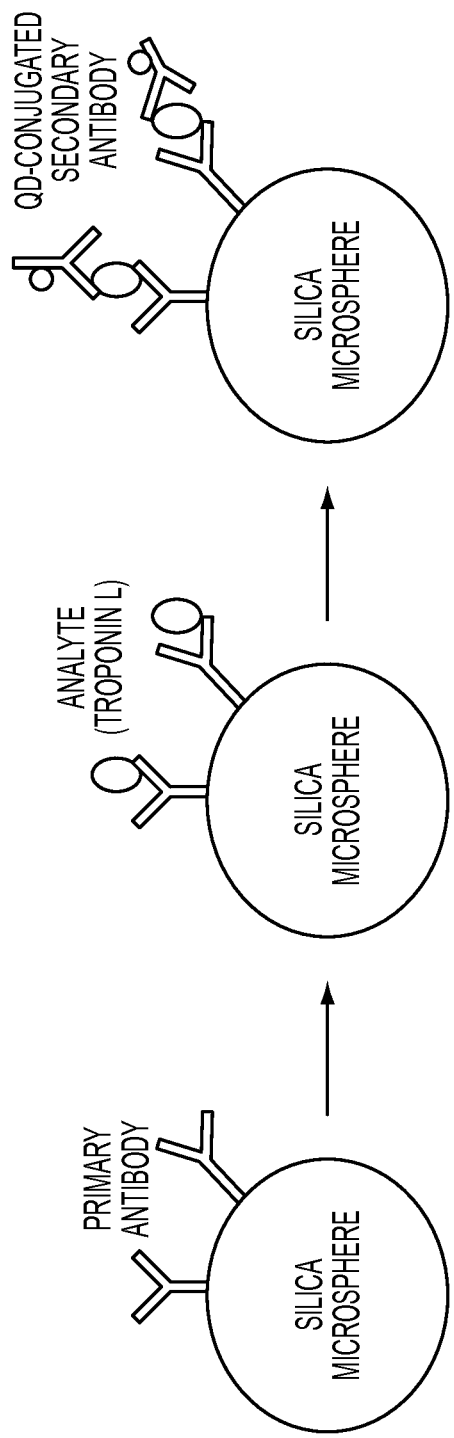
FIG. 6 is an illustration of a microsphere conjugated to a Troponin I-quantum dot complex.

Silica microspheres are conjugated to an antibody that specifically binds to Troponin I. A sample containing an amount of Troponin I is contacted with the silica microspheres, whereupon Troponin I specifically binds to the antibody-microsphere complex. A complex comprised of a second antibody specific to Troponin I and a quantum dot is contacted with the microsphere-Troponin I complex, whereupon the quantum dot-antibody complex specifically binds to the microsphere-Troponin I complex to form microspheres conjugated to a Troponin I-quantum dot complex (FIG. 6). The microspheres are suspended in phosphate buffer and added to an apparatus of the present invention. The suspension of microspheres flows through the channels of the apparatus and the microspheres are concentrated in a well, while the phosphate buffer is wicked away and absorbed into filter paper. The concentrated microspheres are imaged using a CCD camera and a laser, and the amount of Troponin I conjugated to the microspheres is quantified.

Example 2

Quantification of Streptavadin-Biotin Complex in a Sample

Figure 7:
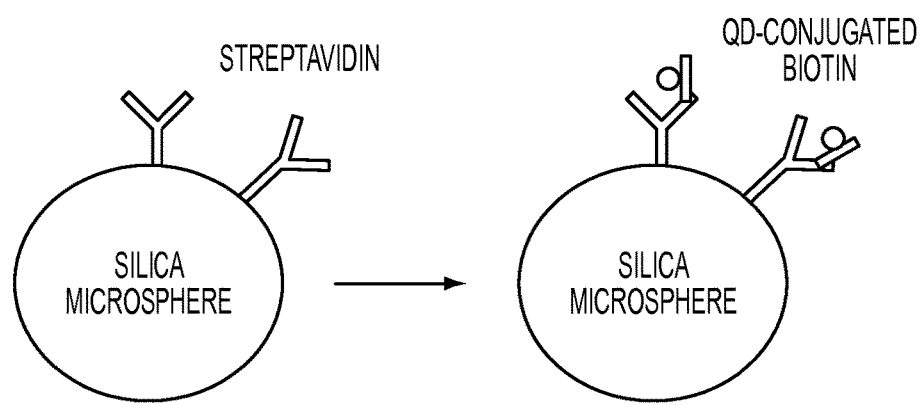
FIG. 7 is an illustration of a microsphere conjugated to a streptavidin-biotin-quantum dot complex.

Silica microspheres are conjugated to Streptavadin. A sample containing an amount of biotin conjugated to a quantum dot is contacted with the microsphere-streptavadin complex, whereupon the quantum dot-biotin specifically binds to the microsphere-streptavadin complex to form microspheres conjugated to a streptavidin-biotin-quantum dot complex (FIG. 7). The microspheres are suspended in phosphate buffer and added to an apparatus of the present invention. The suspension of microspheres flows through the channels of the apparatus and the microspheres are concentrated in a well, while the phosphate buffer is wicked away and absorbed into filter paper. The concentrated microspheres are imaged using a CCD camera and a laser, and the amount of biotin conjugated to the microspheres is quantified.

EQUIVALENTS

Those skilled in the art will recognize, or be able to ascertain using no more than routine experimentation, many equivalents of the specific embodiments of the invention described herein. Such equivalents are intended to be encompassed by the following claims.

INCORPORATION BY REFERENCE

The entire contents of all patents, published patent applications, and other references cited herein are hereby expressly incorporated herein in their entireties by reference.

The invention claimed is:

1. A method for detecting at least one analyte in a fluid sample, the method comprising:
    adding a labeled moiety that specifically binds to an analyte to a fluid sample;
    suspending solid support substrates conjugated to an unlabeled moiety that specifically binds to the analyte in the fluid sample;
    providing a device comprising:
        an absorbent pad;
        a funnel comprising:
            a wide end; and
            a narrow end above and adjacent to the absorbent pad; and
        a sample-loading region in communication with the wide end of the funnel via a non-absorbent lateral channel in between the sample-loading region and the wide end of the funnel;
    introducing the fluid sample into the sample loading region of the device;
    capturing the solid support substrates in a reduced sample volume in the funnel; and
    detecting the labeled moiety bound to the analyte that is, in turn, bound to the unlabeled moiety in the region of the captured solid support substrates when an analyte is present in the sample,
    wherein the presence of the labeled moiety in the region of the captured solid support substrates is indicative of both the labeled and unlabeled moieties binding to the analyte.

2. The method of claim 1, wherein the sample volume is reduced by the absorbent pad removing at least a portion of a carrier liquid from the sample.

3. The method of claim 1, wherein the label is a quantum dot.

4. The method of claim 1, wherein the amount of analyte is quantified.

5. The method of claim 1, further comprising detecting the presence of a plurality of analytes in the sample via a plurality of uniquely labeled moieties and a plurality of unlabeled moieties conjugated to the support substrates.

6. The method of claim 5, wherein the unique labels are different sized quantum dots.

7. The method of claim 1, wherein the solid support substrates are microspheres.

8. The method of claim 7, wherein the microspheres are selected from the group consisting of polystyrene (PS) microspheres, poly(methyl methacrylate) (PMMA) microspheres, silica microspheres, glass microspheres, ceramic microspheres, magnetic microspheres, and paramagnetic microspheres.

9. The method of claim 7, wherein the microspheres have a diameter between 0.5 µm to 5 µm.

10. The method of claim 7, wherein the microspheres have a diameter of 1 µm.

11. The method of claim 1, wherein the device further comprises:
    an imaging window above the funnel.

12. A device comprising:
    an absorbent pad;
    a funnel comprising a wide end that tapers to a narrow end above and adjacent to the absorbent pad; and
    a sample-loading region in communication with the wide end of the funnel via a non-absorbent lateral channel in between the sample loading region and the wide end of the funnel, the sample-loading region configured to receive a fluid sample.

13. The device of claim 12, further comprising:
    an imaging window above the funnel.

* * * * *